US009320774B2

(12) United States Patent
Lai et al.

(10) Patent No.: US 9,320,774 B2
(45) Date of Patent: Apr. 26, 2016

(54) METHOD FOR REDUCING RADIO-RESISTANCE OF PROSTATE CANCER CELLS AND/OR TREATING PROSTATE CANCER

(71) Applicant: CHINA MEDICAL UNIVERSITY, Taichung (TW)

(72) Inventors: Chih-Ho Lai, Taichung (TW); Yu-Hsin Lin, Taichung (TW); Cheng-Kuo Lai, Taichung (TW); Chia-Shuo Chang, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 106 days.

(21) Appl. No.: 14/262,512

(22) Filed: Apr. 25, 2014

(65) Prior Publication Data

US 2015/0202254 A1 Jul. 23, 2015

(30) Foreign Application Priority Data

Jan. 22, 2014 (TW) ............................. 103102246 A

(51) Int. Cl.

| | |
|---|---|
| ***A61K 9/14*** | (2006.01) |
| ***A61K 38/16*** | (2006.01) |
| ***A61K 38/36*** | (2006.01) |
| ***A61P 35/00*** | (2006.01) |
| ***B82Y 5/00*** | (2011.01) |
| ***A61K 9/16*** | (2006.01) |
| *A61N 5/10* | (2006.01) |

(52) U.S. Cl.

CPC ............ *A61K 38/164* (2013.01); *A61K 9/1641* (2013.01); *A61N 2005/1098* (2013.01)

(58) Field of Classification Search

None

See application file for complete search history.

(56) References Cited

FOREIGN PATENT DOCUMENTS

KR 10-2012-0089892 8/2012

OTHER PUBLICATIONS

Lai et al, Nanomedicine, 2014, vol. 9, pp. 803-817.*
Shang et al, Medical Science Monitor, 2014, vol. 20, pp. 2504-2507.*
Gan et al (Colloids and Surfaces B: Biointerfaces, 2007, vol. 59, pp. 24-34).*
Lin et al., "Cholesterol Depletion Reduces Entry of Campylobacter jejuni Cytolethal Distending Toxin and Attenuates Intoxication of Host Cells," Infection and Immunity, Sep. 2011, pp. 3563-3575, vol. 79-No. 9.
Chang, C. S. et al., "Enhancement of radio-sensitivity in prostate cancer stem cells by bacterial genotoxin", National Digital Library of Theses and Dissertations in Taiwan, 2012.
Jinadasa, R. N. et al., "Cytolethal distending toxin: a conserved bacterial genotoxin that blocks cell cycle progression, leading to apoptosis of a broad range of mammalian cell lineages", Microbiology, Jul. 2011;, vol. 157, pp. 1851-1875.
Chung, C. C. et al., "Prepartion of amoxicillin-loaded Chitosan/ Heparin Nanoparticles by Water-in-oil Emulsification for Treating Helicobacter pylori", China Medical University, pp. 1-4. (English Abstract), 2007.

* cited by examiner

*Primary Examiner* — Karen Canella

(74) *Attorney, Agent, or Firm* — Ping Wang; Andrews Kurth LLP

(57) ABSTRACT

A method for reducing the radio-resistance of prostate cancer cells in a subject in need thereof, comprising administering to the subject an effective amount of an active component, wherein the active component is a nanoparticle of a carrier encapsulated with cytolethal distending toxin subunit B (CdtB).

10 Claims, 2 Drawing Sheets

METHOD FOR REDUCING RADIO-RESISTANCE OF PROSTATE CANCER CELLS AND/OR TREATING PROSTATE CANCER

CROSS-REFERENCE TO RELATED APPLICATIONS

This application claims the benefit of Taiwanese Patent Application No. 103102246, filed on Jan. 22, 2014, in the Taiwan Intellectual Property Office, the disclosure of which is incorporated herein in its entirety by reference.

BACKGROUND OF THE INVENTION

1. Field of the Invention

The present invention relates to the treatment of prostate cancer, and in particular, relates to a method for treating prostate cancer or reducing the radio-resistance of prostate cancer cells in a subject, wherein the method comprises administering to a subject in need an effective amount of a medicament comprising an active component. The active component is a nanoparticle of a carrier encapsulated with cytolethal distending toxin subunit B (CdtB). The medicament could be used in combination with radiation therapy to provide an outstanding effect on treating prostate cancer.

2. Description of the Related Art

The prostate is a male-specific genital organ. Prostate cancer has become one of the most common cancers in the male population worldwide. The occurrence of prostate cancer is related to age. Along with changes in eating habits, increase in high fatty food intake and increase in average lifespan, the occurrence and mortality of prostate cancer has risen to become one of the top ten most common causes of death from cancer. While the pathology of prostate is unclear, known etiologies include genetics, diet, hormonal and environmental factors. There are usually no symptoms in the early stage of prostate cancer; however, as the tumor invades or blocks the urinary tract or urethral neck, symptoms similar to urinary track blocking occurs. In the advanced stage, symptoms of acute retention of urine, hematuria and aconuresis may appear. In addition, when bone metasis occurs, patients may suffer from symptoms of bone pain, pathological cataclasis, anemia, and paraplegia caused by the compression of the spinal cord.

The common methods for treating prostate cancer include surgery, hormone therapy and radiation therapy. For patients with lymphatic metastasis or bone metastasis, prostate cancer can not be treated effectively because it is difficult to excise all of the metastatic cancer cells with surgery. In addition, surgery is not always recommended for older patients since the postoperative recover time is slower. Because prostate cancer cells in the early stage are androgen-dependent, androgen stimulation is necessary for the growth and division of prostate cancer cells. In the absence of androgen, prostate cancer cells will regress. Therefore, hormone therapies, such as androgen suppression or androgen ablation, are used in clinics to treat prostate cancer. However, because some prostate cancer cells will change into an androgen-independent form after a period of time, such prostate cancer cells can continuously grow despite treatment with androgen suppression or androgen ablation therapy. Therefore, hormone therapy cannot effectively treat prostate cancer.

In view of the above, both surgery and hormone therapy require an additional therapeutic method, such as radiation therapy. Radiation therapy refers to using a focused radiation beam to damage the DNA structure of prostate cancer cells to stop the growth of cells. Another advantage of radiation therapy is that it can be used to treat patients of any age or health status. The dosage and radiating range can become more precise with the use of an apparatus. However, because prostate cancer cells with radio-resistance will generate and cells can grow continuously even under radiation exposure, radiation therapy is less effective in the late stages of treatment.

In view of the limited therapeutic effect of current treatments for prostate cancer, it is important to provide one method or medicament to effectively treat prostate cancer, especially to reduce the radio-resistance of prostate cancer cells and elevate the cure rate of prostate cancer.

The inventors of the present invention found that a nanoparticle of a carrier encapsulated with cytolethal distending toxin subunit B (CdtB) can increase the radiation sensitivity of the prostate cancer cells with radio-resistance so as to reduce the radio-resistance of said prostate cancer cells. Radiation therapy can be used in combination with a carrier encapsulated with cytolethal distending toxin subunit B to provide an increased therapeutic efficacy and reduce the recurrence of prostate cancer in patients. Such treatment option would benefit the elderly or patients who are not suitable for surgery.

SUMMARY OF THE INVENTION

An objective of the present invention is to provide a use of an active component in the manufacture of a medicament for reducing the radio-resistance of prostate cancer cells, wherein the active component is a nanoparticle of a carrier encapsulated with cytolethal distending toxin subunit B (CdtB).

Another objective of the present invention is to provide a use of an active component in the manufacture of a medicament for treating prostate cancer, wherein the active component is a nanoparticle of a carrier encapsulated with cytolethal distending toxin subunit B and the medicament is used in combination with a radiation therapy.

Yet another objective of the present invention is to provide a method for reducing the radio-resistance of prostate cancer cells in a subject, comprising administering to the subject an effective amount of an active component, wherein the active component is a nanoparticle of a carrier encapsulated with CdtB.

Yet another objective of the present invention is to provide a method for treating prostate cancer in a subject, comprising simultaneously or separately administering to the subject radiation therapy and an effective amount of an active component, wherein the active component is a nanoparticle of a carrier encapsulated with CdtB.

Yet another objective of the present invention is to provide a pharmaceutical composition for reducing the radio-resistance of prostate cancer cells, comprising an effective amount of an active component, wherein the active component is a nanoparticle of a carrier encapsulated with CdtB.

Yet another objective of the present invention is to provide a pharmaceutical composition for treating prostate cancer, comprising an effective amount of an active component, wherein the pharmaceutical composition is to be used in combination with a radiation therapy, and the active component is a nanoparticle of a carrier encapsulated with CdtB.

The detailed technology and preferred embodiments implemented for the present invention are described in the following paragraphs accompanying the appended drawings for people skilled in this field to well appreciate the features of the claimed invention.

DETAILED DESCRIPTION OF THE INVENTION

Figure 1A:
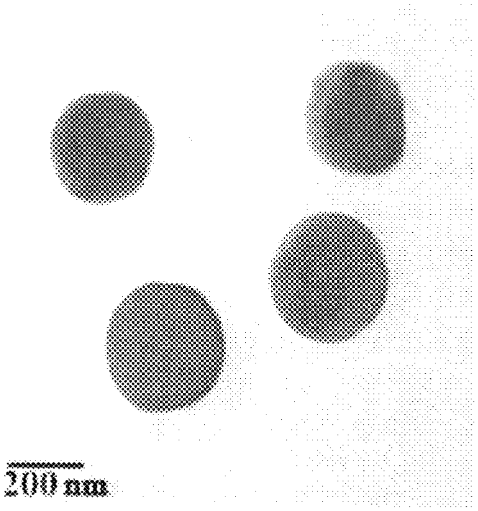
FIG. 1A is a picture showing the nanoparticles of a carrier encapsulated with CdtB according to an embodiment of the present invention.

The following will describe some embodiments of the present invention in detail. However, without departing from the spirit of the present invention, the present invention may be embodied in various embodiments and should not be limited to the embodiments described in the specification. In addition, unless otherwise stated herein, expressions "a", "the", and the like recited in this specification (especially in the claims) should include both the singular and plural forms. Furthermore, the term "effective amount" used in this specification refers to the amount of the compound that can at least partially alleviate the condition that is being treated in a suspected subject when administered to the subject. The term "subject" used in this specification refers to a mammalian, including human and non-human animals.

*Campylobacter jejuni* is one of the major pathogenic bacteria causing human enterogastritis. It has been proven that cytolethal distending toxin (Cdt) plays a very important role in the pathogenic progress of *Campylobacter jejuni*. This toxin could make cells swell and stop at the Gap 2 phase/Mitosis phase (G2/M phase), and cause cell apoptosis. The Cdt is a holotoxin, which consists of three subunits, including CdtA, CdtB, and CdtC. The CdtA and CdtC serve the function of connecting to the cell membrane. The CdtB is a subunit responsible for enzyme activity in Cdt, and has the activity of type I deoxyribinuclease (DNase I) which could damage DNA and pause cell cycle.

The inventors of the present invention found that the nanoparticle of a carrier encapsulated with CdtB is useful in increasing the sensitivity of radio-resistant prostate cancer cells to radiation and thus could reduce the radio-resistance of the prostate cancer cells. A combined use of the nanoparticle of a carrier encapsulated with CdtB and radiation can provide a significant effect on treating prostate cancer.

Therefore, the present invention relates to the applications of a nanoparticle of a carrier encapsulated with CdtB on treating prostate cancer, including the use of he nanoparticle of a carrier encapsulated with CdtB in the manufacture of a medicament for reducing the radio-resistance of prostate cancer cells which are resistant to radiation and/or for treating prostate cancer; administering to a subject in need a nanoparticle of a carrier encapsulated with CdtB to reduce the radio-resistance of prostate cancer cells in the subject and/or treat prostate cancer; and providing a pharmaceutical composition comprising a nanoparticle of a carrier encapsulated with CdtB, wherein the pharmaceutical composition is used for reducing the radio-resistance of the prostate cancer cells in a subject or used in combination with a radiation therapy to treat prostate cancer.

The CdtB involved in the present invention can be cloned and purified from *Campylobacter jejuni*. The method can be seen in Lin et al., Cholesterol depletion reduces entry of *Campylobacter jejuni* cytolethal distending toxin and attenuates intoxication of host cells, *Infect. Immun.* 79(9), 3563-3575 (2011), which is entirely incorporated herein for reference.

Over recent years, nanoparticles have been applied to various fields, such as the biomedical, optics and electronics. In many medical studies, nanoparticles have been used to encapsulate and deliver medicaments due to its small particle size. In the present invention, the CdtB is in the form of a nanoparticle.

In the present invention, the carrier that is used to encapsulate CdtB is a biocompatible material. For example, the carrier may be one or more biocompatible materials selected from the group consisting of chitosan, heparin, polyglutamic acid, tripolyphosphate, polyacrylic acid and polyethylene glycol-chitosan. In some embodiments of the present invention, chitosan and heparin are used for encapsulating CdtB to provide a desired nanoparticle.

The nanoparticle of a carrier encapsulated with CdtB of the present invention can be prepared by any suitable method. For example, in one embodiment of the present invention, the desired nanoparticle could be provided by mixing the CdtB and the carrier material in room temperature through a simple ionic gelation method.

The size of the nanoparticle of a carrier encapsulated with CdtB of the present invention is usually not greater than 1000 nm, and preferably not greater than 500 nm. Optionally, the size of the nanoparticle could be adjusted by changing the relative amount ratio of the carrier and CdtB. Generally, a higher relative amount of CdtB would provide a bigger nanoparticle. For example, when using 0.2 ml heparin solution (2.0 mg/ml) and 2 ml chitosan solution (1.5 mg/ml) as the carrier constituent and using 0.2 ml CdtB with the concentration of 4.0 mg/ml, 8.0 mg/ml, or 16.0 mg/ml, the average size of the obtained nanoparticles were about 300 nm, about 400 nm and about 800 to 900 nm, respectively.

The nanoparticle of a carrier encapsulated with CdtB of the present invention can effectively inhibit the growth of the radio-resistant prostate cancer cells and increase the sensitivity of the radio-resistant prostate cancer cells to radiation. Without being limited by theory, it is believed that CdtB can effectively inhibit the growth of prostate cancer cells based on its effect on the DNA of the cancer cells. Because of the high duplication ability and more DNA content of the radio-resistant prostate cancer cells, they are easier to be inhibited by CdtB. Therefore, the use of the nanoparticle of a carrier encapsulated with CdtB in combination with a radiation therapy can provide a better effect on treating prostate cancer.

Accordingly, the nanoparticle of a carrier encapsulated with CdtB of the present invention can be used to provide a pharmaceutical composition for reducing the radio-resistance of prostate cancer cells which are resistant to radiation or treating prostate cancer, and/or be used in the manufacture of a medicament for reducing radio-resistance of prostate cancer cells which are resistant to radiation or treating prostate cancer, when the treatment is in combination with a radiation. The pharmaceutical composition or the medicament can be manufactured into a medicament of any suitable form for administration. Depending on the form and purpose of the pharmaceutical composition or medicament, the pharmaceutical composition or medicament may further comprise a pharmaceutically acceptable carrier.

For example, the pharmaceutical composition or the medicament can be manufactured into a form suitable for oral administration, subcutaneous injection, or intravenous injection into a subject. For manufacturing a medicament suitable for oral administration, the pharmaceutical composition or the medicament can comprise a pharmaceutically acceptable carrier which has no adverse influence on the activity of the nanoparticle of a carrier encapsulated with CdtB, such as a solvent, an oily solvent, a diluent, a stabilizer, an absorption delaying agent, a disintegrant, an emulsifier, an antioxidant, a binder, a lubricant, and a moisture absorbent. The medicament can be prepared as a formulation for the oral administration by any suitable method, such as a tablet, a capsule, a granule, powder, a fluid extract, a solution, a syrup, a suspension, an emulsion, a tincture, etc.

As for a medicament suitable for subcutaneous injection or intravenous injection, the medicament or the pharmaceutical composition manufactured from the nanoparticle of a carrier encapsulated with CdtB may comprise one or more components, such as an isotonic solution, a saline buffer solution (e.g. a phosphate buffer solution or a citrate buffer solution), a solubilizer, an emulsifier, other carriers, etc., to manufacture the medicament as an intravenous injection, an emulsion intravenous injection, a powder injection, a suspension injection, a powder-suspension injection, etc.

In addition to the above adjuvants, the medicament or the pharmaceutical composition manufactured from the nanoparticle of a carrier encapsulated with CdtB may comprise other additives, such as a flavoring agent, a toner, a coloring agent, etc. to enhance the taste and visual appeal of the resultant medicament or composition. To improve the storability of the medicament or the pharmaceutical composition, a suitable amount of a preservative, a conservative, an antiseptic, an anti-fungus reagent, etc. may also be added. Furthermore, the medicament or the pharmaceutical composition may comprise one or more other active components or be used in combination with a medicament comprising the one or more active components to further enhance the efficacy of the medicament or the composition or to increase the application flexibility and adaptability of the medicament or pharmaceutical composition of the present invention, as long as the other active components have no adverse effect on the nanoparticle of a carrier encapsulated with CdtB.

In addition, the medicament or the pharmaceutical composition manufactured from the nanoparticle of a carrier encapsulated with CdtB can be simultaneously or separately administered with a radiation therapy to the subject in need of such treatment. For example, the medicament or pharmaceutical composition could be administered by oral administration or injection. The radiation therapy could be performed immediately or after a time interval (usually after 24-48 hours). Alternatively, radiation therapy could be performed a while before the oral administration or injection of the medicament or the pharmaceutical composition, and be performed again after the oral administration or injection.

The medicament or the pharmaceutical composition manufactured from the nanoparticle of a carrier encapsulated with CdtB can be administered with various administration frequencies, such as once daily, several times a day, or once every few days, etc. For example, when applied to the human body for reducing the radio-resistance of prostate cancer cells, the nanoparticle of a carrier encapsulated with CdtB is administrated at a dosage ranging from about 1 mg (as CdtB)/kg-body weight to about 5 mg (as CdtB)/kg-body weight per day, and preferably from about 2.5 mg (as CdtB)/kg-body weight to about 4 mg (as CdtB)/kg-body weight per day, wherein the unit "mg/kg-body weight" means the dosage required per kg-body weight of the treated subject. When the medicament or the pharmaceutical composition manufactured from the carrier encapsulated with CdtB is administered to a subject once a day in combination with a radiation therapy to treat prostate cancer, the nanoparticle of a carrier encapsulated with CdtB is administrated at an amount ranging from about 1 mg (as CdtB)/kg-body weight to about 5 mg (as CdtB)/kg-body weight, and preferably about 1.5 mg (as CdtB)/kg-body weight to about 3 mg (as CdtB)/kg-body weight. For example, a combination of the medicament or the pharmaceutical composition and the radiation therapy can provide an excellent treatment efficacy as the medicament or pharmaceutical composition is administered at an amount of about 2.5 mg (as CdtB)/kg-body weight once a day. However, for patients with acute conditions, the dosage can be increased to several times or several tens of times, depending on the practical requirements.

The present invention also provide a method for reducing the radio-resistance of prostate cancer cells which are resistant to radiation in a subject, comprising administering to the subject an effective amount of an active component, wherein the active component is the nanoparticle of a carrier encapsulated with CdtB. The types of carrier and the applied form and the dosage of the nanoparticle of a carrier encapsulated with CdtB are all as described hereinabove.

The present invention also provides a method for treating prostate cancer in a subject, comprising administering to the subject an effective amount of an active component and radiation therapy, wherein the active component is a nanoparticle of a carrier encapsulated with CdtB. The types of carriers, applied forms and dosages of the nanoparticle of a carrier encapsulated with CdtB are all as described above.

The present invention will be further illustrated in details with specific examples as follows. However, the following examples are provided only for illustrating the present invention, and the scope of the present invention is not limited thereby.

Example 1

Preparation of Nanoparticles of a Carrier Encapsulated with CdtB

First, 0.2 ml CdtB (4.0 mg/ml) and 0.2 ml heparin solution (2.0 mg/ml) were mixed to provide a mixture. The mixture was stirred in 2 ml chitosan solution (1.5 mg/ml) at room temperature for 10 minutes. Then, the mixture was centrifuged at 15,000 g for 50 minutes, and the supernatant liquid was removed and the precipitates (i.e. the carrier encapsulated with CdtB particles) were collected.

Figure 2:
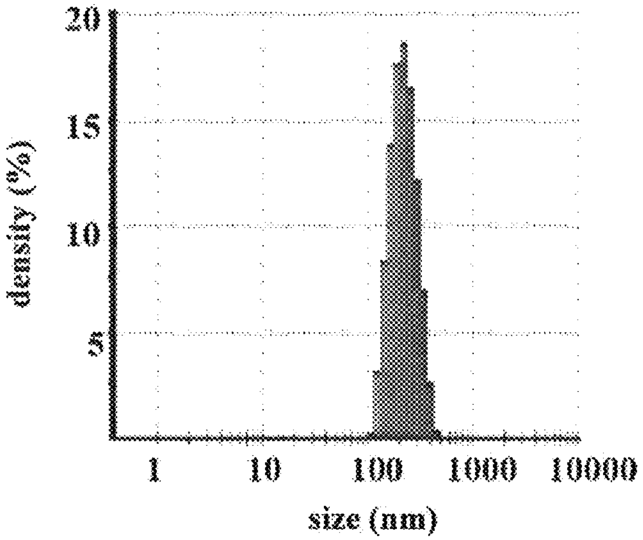
FIG. 2 is a bar diagram showing the particle size of the nanoparticle of a carrier encapsulated with CdtB according to an embodiment of the present invention, wherein the vertical axis represents the number (%) of the nanoparticles, and the horizontal axis represents the particle size (nm) of the nanoparticles.

The collected precipitates were dissolved in deionized water to obtain a suspension. The form of the particles in the suspension was observed through a transmission electron microscope (TEM) and the distribution of the particle size was analyzed by dynamic light scattering spectrometer (Zetasizer ZS90, Malvern, United Kingdom). The results are shown in FIGS. 1A and 2. As shown in FIGS. 1A and 2, the carrier encapsulated with CdtB particles were smaller than 500 nm, belonging to nanoparticles, and the average particle size of the carrier encapsulated with CdtB particles was about 300 nm (hereinafter referred to as "the nanoparticle of a carrier encapsulated with CdtB").

Figure 1B:
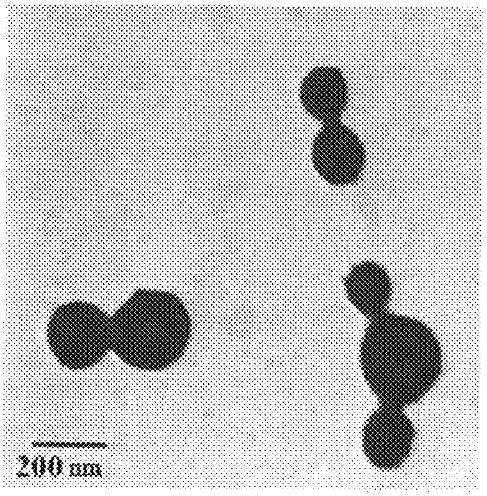
FIG. 1B is a picture showing the nanoparticles of a carrier without being encapsulated with CdtB.

In addition, particles containing no CdtB were manufactured by the same procedures without using CdtB. The form of the particles in the suspension was observed through a transmission electron microscope (TEM) and shown in FIG. 1B. As showed in FIG. 1B, the particle size of the nanoparticles of a carrier encapsulated without CdtB was about 200 nm to 250 nm.

Example 2

The Cytotoxicity Experiment of the Cancer Cells

To evaluate whether the nanoparticle of a carrier encapsulated with CdtB could affect the viability of the prostate cancer cells, 1-(4,5-dimethylthiazol-2-yl)-3,5-diphenylformazan (MTT) was used in this experiment.

MTT is a soluble tetrazolium salt and can affect the respiratory chain of the mitochondria in live cells. Under the effect of succinate degydrogenase (SDH) and cytochrome c (cyt c), tetrazolium bromide in MTT structure would be a metabolic reduction and an ianthinus formazon with an insoluble crystal would be formed. Because of the absence of the succinate dehydrogenase in dead cells, the MTT can not be reduced, and the formation of the crystal substrate is also considered to be directly proportionate to the number of live cells. Furthermore, the mitochondrion is an organelle which is the most sensitive to the environment, and thus, it can be used as a marker for analyzing cell viability after the medicament treatment.

The prostate cancer cells ($5\times10^3$ cells/well) with radio-resistance (PC3-KD cell line with the DAB2IP gene deletion) were cultured in a 96-well culture plate. After being cultured in an incubator at 5% $CO_2$ at 37□ for 24 hours, the cells were treated individually with the following method: (i) treated with 500 nM nanoparticles of carrier encapsulated without CdtB for 24 hours (hereinafter referred to as a "control group"); (ii) treated with 500 nM nanoparticle of a carrier encapsulated with CdtB for 24 hours (hereinafter referred to as "CdtB nanoparticle group"); (iii) irradiated with 2 gray (Gy) radiation for 3 minutes (hereinafter referred to as "radiation group"); and (iv) treated with 500 nM nanoparticle of a carrier encapsulated with CdtB, and irradiated with 2 Gy radiation for 3 minutes and reacted for 24 hours (hereinafter referred to as "CdtB nanoparticle+radiation group"). After the above treatment, the suspension was removed. Then, 10 μl/well of MTT and 100 μl/well of culture medium were added in the dark for 4 hours. Then, the all culture medium was removed; added 100 μl/well of DMSO in the dark to react for 10 minutes and analyzed the wavelength of 570 nm absorbance. The absorbance of the "control group" (viability is 100%) was used as a control, and the viability of each group were measured. The results are shown in FIG. 3 and Table 1.

TABLE 1

| Group | Cancer cell viability (%) |
|---|---|
| control group | 100 |
| CdtB nanoparticle group | 69.73 |
| radiation group | 95.30 |
| CdtB nanoparticle + radiation | 55.4 |

Figure 3:
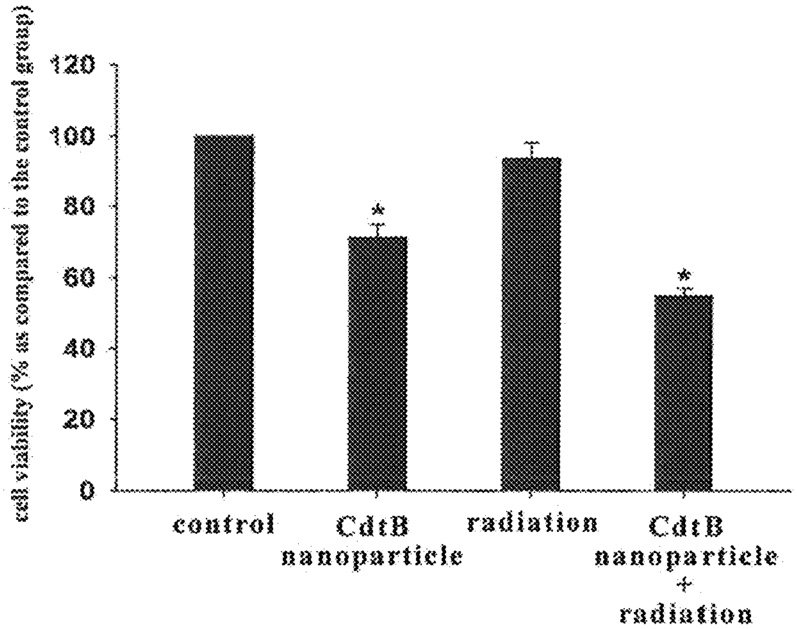
FIG. 3 shows the comparison of the survival rate of the radio-resistant prostate cancer cells treated differently (* represent the p value smaller than 0.01, with a significant difference), wherein the vertical axis represents the cell survival rate (%) as compared to the control group, and wherein the control group is the prostate cancer cells treated with the nanoparticles of a carrier without being encapsulated with CdtB.

According to FIG. 3 and Table 1, the viability of cancer cells in "radiation group" was still up to 95.30%, revealing that the prostate cancer cells had radio-resistance could not be effectively killed by radiation treatment alone. The result of the "CdtB nanoparticle group" showed that the viability of the prostate cancer cells with radio-resistance was reduced to 69.73% when treated with the CdtB nanoparticle alone, indicating that the CdtB nanoparticle was effective in treating prostate cancer cells. The result of the "CdtB nanoparticle+ radiation group" showed the viability of prostate cancer cells with radio-resistance was reduced to 55.4% when treated with "CdtB nanoparticle" in combination with "radiation," indicating that the "CdtB nanoparticle" had the ability to reduce the radio-resistance of prostate cancer cells, and thus, can reduce the viability of cancer cells from 69.73% to 55.4% when treated with "CdtB nanoparticle" in combination with "radiation" rather than treated with "CdtB nanoparticle" alone.

What is claimed is:

1. A method for reducing the radio-resistance of prostate cancer cells in a subject in need thereof, comprising administering to the subject an effective amount of an active component, wherein the active component is a nanoparticle of a carrier encapsulated with cytolethal distending toxin subunit B (CdtB), and the carrier comprises chitosan and heparin.

2. The method according to claim 1, wherein the nanoparticle has a particle size not greater than 1000 nanometers.

3. The method according to claim 2, wherein the nanoparticle has a particle size not greater than 500 nanometers.

4. The method according to claim 1, wherein the nanoparticle has an average particle size of about 300 nanometers to about 400 nanometers.

5. The method according to claim 1, wherein the cytolethal distending toxin subunit B protein is cloned from *Campylobacter jejuni*.

6. A method for treating prostate cancer in a subject in need thereof, comprising simultaneously or separately administering to the subject a radiation therapy and an effective amount of an active component, wherein the active component is a nanoparticle of a carrier encapsulated with cytolethal distending toxin subunit B (CdtB), and the carrier comprises chitosan and heparin.

7. The method according to claim 6, wherein the nanoparticle has a particle size not greater than 1000 nanometers.

8. The method according to claim 7, wherein the nanoparticle has a particle size not greater than 500 nanometers.

9. The method according to claim 6, wherein the nanoparticle has an average particle size of about 300 nanometers to about 400 nanometers.

10. The method according to claim 6, wherein the cytolethal distending toxin subunit B protein is cloned from *Campylobacter jejuni*.

* * * * *